(12) United States Patent
Poezevera et al.

(10) Patent No.: US 6,773,404 B2
(45) Date of Patent: Aug. 10, 2004

(54) DISCRIMINATING BETWEEN AN AWAKE PHASE AND A SLEEP PHASE OF A PATIENT IN AN ACTIVE IMPLANTABLE MEDICAL DEVICE

(75) Inventors: Yann Poezevera, Courcouronne (FR); Marcel Limousin, Paris (FR)

(73) Assignee: ELA Medical S.A., Montrouge (FR)

( * ) Notice: Subject to any disclaimer, the term of this patent is extended or adjusted under 35 U.S.C. 154(b) by 78 days.

(21) Appl. No.: 10/310,689

(22) Filed: Dec. 5, 2002

(65) Prior Publication Data

US 2003/0163059 A1 Aug. 28, 2003

(30) Foreign Application Priority Data

Dec. 7, 2001 (FR) ............................................ 01 15867

(51) Int. Cl.[7] ........................... A61B 5/08; A61B 5/103; A61B 5/00; A61B 5/117
(52) U.S. Cl. ...................... 600/534; 600/536; 600/529; 600/595; 600/301
(58) Field of Search ................................ 600/534, 529, 600/532, 533, 300, 301, 481, 536, 547, 544, 595

(56) References Cited

U.S. PATENT DOCUMENTS

| | | | |
|---|---|---|---|
| 5,280,791 A | * 1/1994 | Lavie | 600/509 |
| 5,299,118 A | * 3/1994 | Martens et al. | 600/509 |
| 5,476,483 A | 12/1995 | Bornzin et al. | 607/17 |
| 5,622,428 A | 4/1997 | Bonnet | 128/630 |
| 6,188,927 B1 | 2/2001 | Lu et al. | 607/17 |
| 6,306,088 B1 | * 10/2001 | Krausman et al. | 600/301 |

FOREIGN PATENT DOCUMENTS

| | | | |
|---|---|---|---|
| EP | 0 719 568 A1 | 7/1996 | .......... A61N/1/365 |
| EP | 0 940 155 A2 | 9/1999 | ............ A61N/1/36 |

\* cited by examiner

Primary Examiner—Mary Beth Jones
Assistant Examiner—Navin Natnithithadha
(74) Attorney, Agent, or Firm—Orrick, Herrington & Sutcliffe LLP

(57) ABSTRACT

An active medical device having an improved discrimination between an awake phase of a patient and a sleep phase of a patient. This device measures a physiological parameter of a patient, delivers a physiological signal with a slow time response variation, in particular a signal of minute-ventilation (signal MV), and detects whether the patient is in a phase of awakening or sleep. An average (VE) of the signal MV is calculated over a given number of respiratory cycle and compared with a predetermined threshold (Threshold MV), such that a first state of awakening is determined when the average is higher than the threshold, and a first state of sleep is determined in the contrary case. The device also measures patient activity (signal G), using a signal having a short response time. The activity signal is compared with a predetermined threshold (Threshold G), and a second state of the patient is determined to be an awakening phase when the activity signal is higher than the threshold, and a sleep state in the contrary case. Detecting the phases of awakening and sleep also includes comparing the first state of awakening/sleep to the second state of awakening/sleep, and in the event of a discordance between these states, the response time of the physiological signal processing is modified, in particular by reducing the number of respiratory cycles over which the average MV signal ($VE_{128}$, $VE_{64}$) is calculated.

20 Claims, 1 Drawing Sheet

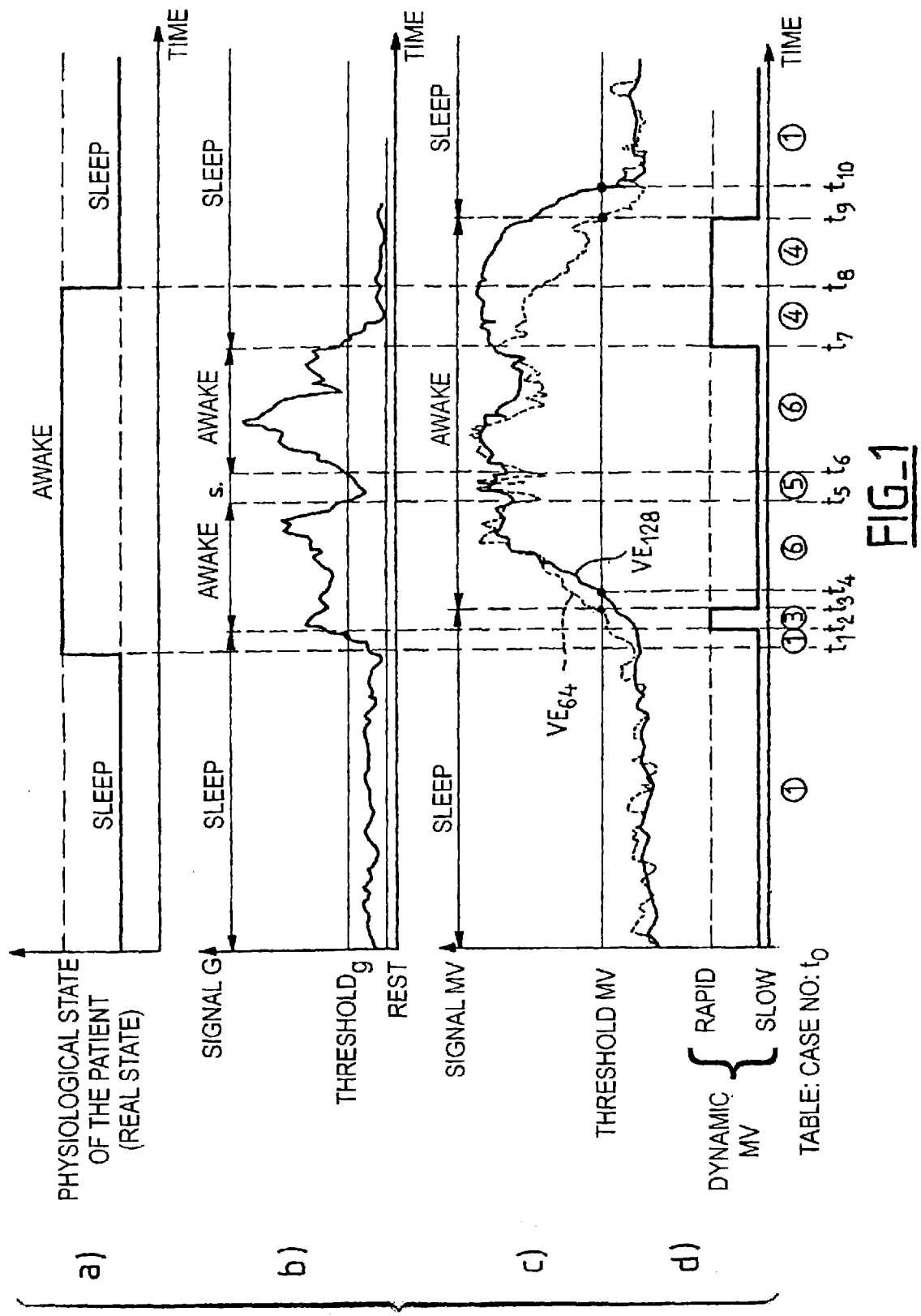

DISCRIMINATING BETWEEN AN AWAKE PHASE AND A SLEEP PHASE OF A PATIENT IN AN ACTIVE IMPLANTABLE MEDICAL DEVICE

FIELD OF THE INVENTION

The present invention relates to "active medical devices" as such devices are defined by the Jun. 14, 1993 Directive 93/42/CEE of the Council of the European Communities. Although described in the case of implantable active medical devices, such as cardiac pacemakers, defibrillators and/or cardiovertors devices that are able to deliver to the heart low energy pulses for treating disorders of the heartbeat rate, it should be understood that the invention is not limited to such implantable active medical devices, but is rather directly applicable to many types of diagnostic and/or therapeutic active medical devices.

BACKGROUND OF THE INVENTION

The invention more particularly relates to improvements in the diagnosis of disorders that occur when a patient is asleep. This includes disorders of a cardiac nature, and disorders of a respiratory nature, including disorders such as apnea or hypopnoea revealing in particular a pathology known as "sleep apnea syndrome" (SAS). An apnea is generally defined as being a respiratory pause of a duration greater than 10 seconds and occurring during a phase of sleep of the patient (because an apnea during phase of awakening (i.e., when the patient is awake) cannot in any case be the cause of an SAS condition).

A diagnosis of sleep-related disorders implies that the device can effectively discriminate between when the patient is awake (i.e., in an awake phase) and asleep (i.e., in a sleep phase). An analysis of the patient's respiration rate and/or cardiac rate to be carried out for this diagnosis is/are to be made only during a sleep phase.

The importance of a precise discrimination between sleep and awakening is made even more necessary when the device not only operates a diagnostic function but also applies a therapy: The therapy should be applied only during a sleep phase, and any therapy must be inhibited if the apnea occurs during an awakening phase, because such an apnea is a normal event and not pathological.

According to published European Patent Application EP-A-0 719 568 and its counterpart U.S. Pat. No. 5,622,428, commonly assigned to the assignee of this invention, Ela Médical, it is known to operate a discrimination between awakening and sleep by analysis of a physiological signal, namely the minute-ventilation (MV) parameter representative of the periodicity and amplitude of successive respiratory cycles of the patient. The minute-ventilation is a known parameter that is defined as the product of the amplitude by the frequency of the respiration. The reader is referred to U.S. Pat. No. 5,622,428, the disclosure of which is expressly incorporated herein by reference in its entirety, for additional details. More precisely, EP-A-O 719 568 and U.S. Pat. No. 5,622,428 disclose a sensor MV which includes circuits to measure an impedance related to the patient's respiratory activity and process that impedance measurement to produce a series of successive samples of a minute ventilation signal (referred to herein as "signal MV") and to calculate an average of the samples over a given number of respiratory cycles, for example, the last 128 cycles, and to compare this average value with a reference value, for example, the average of signal MV over the last 24 hours. Indeed, the circadian variation of the frequency and amplitude of the respiratory cycles is well reproduced by the signal MV. The calculation of the average ventilation over 24 hours thus makes it possible to operate a satisfactory discrimination between ventilation of an awake patient and a ventilation of an asleep patient.

However, the signal MV has a natural variability because it is at the same time of a vegetative and of a controlled nature of the respiratory system. Thus, for example, none of the sighs, the voluntary apnea during speech, and the apnea of the sleep, that appear in an instantaneous measurement is representative of an effective level of the current minute-ventilation, i.e., of the level making it possible to analyse the state of activity of the patient.

For this reason the diagnosis of awakening or sleep can be operated in a reliable way only if one determines the current minute-ventilation by use of an average of a relatively high number of respiratory cycles, typically the last 128 respiratory cycles; this sample set is used in order to eliminate the natural variation as well as the artifacts that are related to the measuring equipment.

The consequence of proceeding in this manner is that, when the patient state changes based on the respiratory activity passing from a sleep phase to an awakening phase, the system of detection presents a certain delay at the diagnosis of the awakening. This is because the average value of signal MV needs to become higher than the reference threshold to make it possible to discriminate between awakening and sleep phases. The problem arises in the same way at the time of the passage of the patient state from an awakening state to a sleep phase. In certain cases, this delay is not awkward. For example, the progressive reduction in the cardiac stimulation frequency during sleep, intended to respect the natural physiology of the patient, does not require a significant reactivity.

On the other hand, the monitoring of an event or the follow-up of a parameter occurring exclusively during the sleep phase (respiratory disorder such as sleep apnea, particular cardiac events) can require a great reactivity in order not to miss the event. This is particularly significant when the patient has a de-structured sleep that presents many awakenings during the night, especially if these awakenings are, precisely, caused by the events which one seeks to detect (a typical example being sleep apnea).

Moreover, if the incidence of the analysed parameter is calculated as from the time of total sleep (as in the case of the calculation of a sleep apnea syndrome, which is defined as a minimum number of apnea per hour of sleep), it is all the more necessary to quickly identify the transitions between phases of awakening and sleep to evaluate correctly the time of total sleep and to operate a correct diagnosis. Such is the case, for example, the case when one defines that there is SAS when the apnea index exceeds a predetermined threshold, for example, more than ten apnea per hour of sleep.

OBJECTS AND SUMMARY OF THE INVENTION

It is, therefore, an object of the present invention to mitigate the disadvantages due to the delay in the diagnosis of an awakening phase or a sleep phase during a phase shift, a delay resulting from the need for averaging the signal MV over a relatively large number of respiratory cycles.

It should be understood, however, that the invention is not limited to the devices proceeding by analysis of a physiological signal such as minute-ventilation, nor even of a signal representative of the respiratory activity of a patient. It is rather the most current configuration, and the present description will be made within the framework of this example. However, the invention applies equally as well to devices implementing other types of physiological sensors having a slow evolution of the signal over time, such as pH or temperature sensors, sensors of oxygen saturation of blood, etc.

It is another object of the invention to improve the reactivity of the active medical device to changes between phases of awakening and sleep, thus to improve the diagnosis, to avoid the false positive detection (i.e., detection of an apnea or an artifact at the beginning of a phase of awakening), and to avoid a false negative detection (non-detection of an apnea at the beginning of a phase of sleep).

The invention also has as an object to improve the conditions for triggering delivery of a therapy, to avoid applying a therapy that should be exclusively applied only during phases of sleep and is inappropriate during phases of awakening.

Broadly, the present invention employs an auxiliary sensor having a relatively fast response time, typically a sensor that is responsive to patient activity or acceleration ("sensor G"), having an output signal that makes it possible to detect the movements of the patient. Contrary to the aforementioned sensor MV, the information of this type of auxiliary sensor is not very specific to the phases of awakening or sleep; on the other hand its response is fast so that one can use the output signal delivered by this auxiliary sensor to improve the dynamic of the sensor MV during the phase shifts (change in state between an awakening phase and a sleep phase and vice versa), even if the diagnosis of the phases of awakening or of sleep remains based only on the signal delivered by the sensor MV.

It is certainly known to use jointly the signals delivered by two different sensor types, namely a sensor of effort having a slow response time, measuring a predominantly physiological parameter (typically the sensor MV), and a sensor of activity having a fast response time, measuring a predominately physical parameter (typically an accelerometer sensor G). The European Patent Application EP-A-0 750 920 and its corresponding U.S. Pat. No. 5,722,996, and EP-A-0 770 407 and its corresponding U.S. Pat. No. 5,766, 228, also assigned herewith to Ela Médical, describe devices implementing a combination of such sensors for different purposes, for example, to adapt the control of a cardiac stimulation to the real physiological situation of the patient, (EP-A-0 750 920 and U.S. Pat. No. 5,722,926) or to put out of service (to sleep) in certain situations the measuring equipment in order to reduce the energy consumption of the device (EP-A-0 770 407 and U.S. Pat. No. 5,766,228). In these documents, however, the combination of the different sensors does not have as an aim to operate a discrimination between phases of awakening and sleep, even less to modify, in this context, the analysis of a signal MV according to the information delivered by a sensor of activity. Nevertheless, the disclosures of U.S. Pat. Nos. 5,766,228 and 5,722,926 related to the structure, design, and implementation of the different sensors and their corresponding signal acquisition processing and shaping, are incorporated herein by reference.

One aspect of the present invention is directed to a medical device of the general type described in the EP-A-0 719 568 and U.S. Pat. No. 5,622,428 above mentioned, i.e., including: means for measuring a physiological parameter of a patient related to the patient's effort or cardiac output requirements and delivering a physiological signal that varies relatively slowly over time; and means for detecting the awakening and sleep phases of the patient, the detecting means including: a first comparator means for computing an average of the successive values of the physiological signal over a given number of prior periods, and comparing the average with a predetermined physiological threshold, and means for indicating a first state of the patient as being in an awakening phase when the aforementioned average is higher than the physiological threshold, and for indicating the first state as being in a sleep phase in the contrary case.

According to the present invention, this device also includes: means for measuring the activity of the patient and producing a signal corresponding to the physical activity of the patient having a relatively fast response time; a second comparator means for comparing the activity signal with a predetermined activity threshold; and means for indicating a second state of the patient as being in an awakening phase when the activity signal is higher than the activity threshold, and in a sleep phase in the contrary case. In addition, the aforementioned means for detecting the phases of awakening and sleep of the patient also includes: means for comparing the aforementioned first state (awakening or sleep phase) with the aforementioned second state (awakening or sleep phase); and means for selectively modifying the response time of the aforesaid first comparator means in the event of a discordance between the phases of the aforementioned first and second states.

In a preferred embodiment, the physiological signal is a minute-ventilation signal and the aforementioned prior periods are preceding respiratory cycles.

In a more preferred embodiment, the anticipating means is able to modify, in particular to reduce, and more particularly to reduce by at least 50%, the aforementioned given number of prior periods over which is calculated the aforementioned average of the successive values of the physiological signal.

In a preferred embodiment, the anticipating means is able to selectively reduce the aforementioned number of prior periods when the first state is an awakening phase, the second state is a sleep phase, and the value of the aforementioned average evolves in a decreasing direction, or when the aforementioned first state is a sleep phase, the second state is an awakening phase, and the value of the aforementioned average evolves in a direction that is stable or increasing.

The physical activity signal of the patient having a fast response time is advantageously a signal delivered by an acceleration sensor. It should be understood that the response times of the sensor having a fast response time and the sensor having a slow response time are essentially defined as fast and slow relative to one another (rather than in reference to particular absolute values) and are in accord with the response times of the known devices. However, the fast and slow response times of the sensors employed in the present invention are not to be considered as limited to those of the known prior art response times, but should be considered expansively while preserving the fast and slowness relative to each other.

The invention applies very preferentially if the device includes means for detecting the respiratory sleep disorders, in particular the detection of apnea and the calculation of an apnea index, these means being then activated only when the aforementioned first state is a sleep phase.

The invention can be advantageously implemented in an active implantable medical device of the cardiac pacemaker, defibrillator, cardiovertor and/or multisite type device.

BRIEF DESCRIPTION OF THE DRAWING

Further benefits, features and characteristics of the present invention will become apparent to a person of ordinary skill in the art in view of the following detailed description of the invention, made with in reference to the annexed drawing, which illustrates a series of chronograms explaining the way in which discrimination between awakening and sleep is operated in accordance with a preferred embodiment of this invention.

DETAILED DESCRIPTION OF THE INVENTION

With reference to the drawing FIG. 1, the chronogram of line (a) represents the real physiological state of the patient, who is initially in a sleep phase (SLEEP). At the moment $t_1$ the patient awakens (AWAKE), and this awakening phase has a duration that ends at the moment $t_8$ when the patient enters a new sleep phase (SLEEP).

The chronogram of line (c) represents in full line the signal MV delivered by the minute-ventilation sensor MV, after the minute-ventilation measure was sampled and averaged over the 128 preceding respiratory cycles. This average value is indicated $VE_{128}$ The signal MV is a predominantly physiological parameter obtained by an intrathoracic impedance measurement. This measurement is preferably obtained between two electrodes laid out in the rib cage, or between an electrode (for example, a stimulation electrode, if the implanted device is a cardiac pacemaker) and the case of the device. The impedance is measured by injection of a constant current of a few hundred milliamperes, at a frequency of a few Hertz, typically 8 Hz. This technique is, for example, described in Bonnet JL, et al., "Measurement of Minute-Ventilation with Different DDDr Pacemaker Electrode Configurations," *Pace*, Vol. 21, 98 Part 1, and it is implemented in the rate responsive dual chamber cardiac pacing functionality of the CHORUS RM, TALENT and SYMPHONY brand products sold by Ela Médical Montrouge, France.

The period of sleep is of course diagnosed in an automatic manner, typically starting from the signal delivered by the sensor that is monitoring the respiration rate of the patient. However, although the minute-ventilation signal is generally easiest to use for the monitoring of the respiration rate of the patient, other signals coming from other types of sensors can be used in the alternative to or to complement the use of the sensor MV, for example, a sensor of blood oxygen saturation.

Until now, the transition between awakening and sleep phases was detected by comparing average value $VE_{128}$ with a threshold, indicated "Threshold MV", determined from an average value calculated over 24 hours of signal MV. Thus, in the illustrated example, the awakening of the patient was detected at the moment $t_4$ (reflecting a delay $t_4-t_1$ compared to the real moment of the awakening) and the falling-asleep at the moment $t_{10}$ (reflecting a delay $t_{10}-t_8$ compared to the real moment of falling asleep).

To reduce these delays in the detection of the phase shifts, the invention proposes to use an auxiliary sensor, preferably and typically an acceleration sensor ("sensor G"). The signal delivered directly by the sensor G is then averaged over a relatively short duration (for example, 64 cardiac cycles) in order to eliminate artifacts and any short, non significant, variations. This averaged signal, indicated "signal G" is represented by the curve of the chronogram of the line (b) of FIG. 1. Signal G is then compared with an activity threshold, indicated "Threshold G", which, for example, is fixed at 10% above the value of the base line. The base line corresponds to a rest condition. If signal G exceeds Threshold G, one will define a state of the patient as being in an awakening phase according to the sensor G; in the contrary case, one will define the state as a sleep phase according to the sensor G. The device thus has two state indicators of awaking/sleep, defined starting from the two signals signal MV and signal G. These two states can be concordant or not.

The state of the patient being in an awakening or sleep phase continues to be diagnosed on the basis of signal MV but, according to the situation, the value having to be compared with Threshold MV will be either average $VE_{128}$ (referred to herein as the "slow dynamic") or average $VE_{64}$ calculated over a shorter period, typically over 64 preceding samples (referred to herein as the "fast dynamic").

The evolution of average $VE_{64}$ is illustrated in dotted lines on line (c) of FIG. 1, where one can see that the characteristic presents a form more variable than that of average $VE_{128}$ because the average taken over a shorter period has a larger variability. If the states (awake/sleep) given by the two signals, signal G and signal MV, agree, then the operation of the device is not modified, i.e., the state of awakening or sleep is given starting from signal MV by comparing $VE_{128}$ with Threshold MV (the slow dynamic).

On the other hand, in the event of discordance between the two signals (i.e., they do not produce the same phase), an additional criterion is introduced, which is the trend of the signal MV: decreasing, stable or increasing. This trend is determined by comparison between current value $VE_{128}$ and a value $VE_{128}$ previously calculated. The trend is known as stable if the variation is less than 10%, and otherwise it is deemed as increasing or decreasing, according to the sign of the variation.

When a change of state of the sensor G occurs, and the signal MV indicates an appropriate trend, the operation of the device is modified so as to determine the state as being in an awakening or sleep phase starting not from $VE_{128}$ (slow dynamic), but starting from $VE_{64}$ (fast dynamic) so as to get a greater reactivity. The cases where the dynamic is made fast are summarized by the state table below.

TABLE 1

| State Sensor MV | State Sensor G | Trend Signal MV | Dynamic | Case No. (FIG. 1) |
|---|---|---|---|---|
| Sleep | Sleep | — | Slow | 1 |
| Sleep | Awake | Decrease/Stable | Slow | 2 |
| Sleep | Awake | Increasing | Fast | 3 |
| Awake | Sleep | Decreasing | Fast | 4 |
| Awake | Sleep | Increasing/Stable | Slow | 5 |
| Awake | Awake | — | Slow | 6 |

Referring to the example illustrated on FIG. 1, initially the sensor MV indicates a sleep phase ($VE_{128}$, Threshold MV); as long as the sensor G confirms this phase, the dynamic remains slow. At moment $t_1$, the patient awakes, but none of the two sensors (MV, G) yet crossed a threshold defining a change of state.

At moment $t_2$ the awakening phase is diagnosed by the sensor G, and as the trend of signal MV is increasing, the analysis of signal MV passes to a fast dynamic: it is the signal $VE_{64}$ (and no more $VE_{128}$) that is then compared with Threshold MV.

When, at moment $t_3$ $VE_{64}$ reaches Threshold MV, the two sensors each indicate a state of awakening phase, which is thus confirmed as such to the device, and the dynamic becomes again slow.

At the time of the episode between moments $t_5$ and $t_6$, which can, for example, correspond to a period of short rest, the sensor G indicates a of sleep phase (signal G passes again below Threshold G) but $VE_{128}$ thus remains higher than Threshold MV. As a result, the device continues to consider the state to be awakening—and, trend MV not being decreasing, the dynamic remains unchanged (it remains slow).

The end of the awakening phase is characterized by a period of progressive rest of the patient that leads to the passing into the sleep phase at moment $t_8$. For this period of progressive rest, falling asleep is detected at moment $t_7$ by the sensor G, the trend MV signal being decreasing, and the dynamic becomes fast to be able to detect an apnea that could occur at the beginning of sleep, and being precise on the number of episodes. This fast dynamic is then maintained until confirmation of a sleep state, at moment $t_9$ by the sensor MV, corresponding to the crossing of Threshold MV by signal $VE_{64}$.

Ultimately, the detection of the awakening or sleep phases according to the invention makes it possible to advance the moment of detection of the awakening phase from $t_4$ (as obtained by the prior art) to $t_3$ (as obtained by the invention), and the detection of the sleep phase of $t_{10}$ (with the prior art) with $t_9$ (with the invention).

The invention thus makes it possible to improve in a substantial manner the diagnosis of the disorders occurring during sleep (respiratory and/or cardiac disorders), the corresponding counting of the events and the calculation of the parameters such as the apnea index, while preserving the advantages of calculation starting from a value of signal MV sufficiently averaged to eliminate the natural variations and the artifacts related to the measuring equipment.

It will be noted that the use of signals $VE_{128}$ and $VE_{64}$ is not restrictive, and that it is equally possible to use signals $VE_{64}$ and $VE_{32}$ or $VE_{16}$, etc., in a comparable manner. In addition, it can be advantageous to envisage after each change of the dynamic a period of delay (for example, a duration of X respiratory cycles) or including a hysteresis loop, during which the dynamic is not modified, so as to avoid the undesirable phenomena of oscillations that might occur during changes of the dynamic.

Suitable devices for which the present invention has application include, but are not limited to, for example, the Chorus RM™, Talent™ and Symphony™ brand of implanted cardiac rhythm management devices available from Ela Médical, Montrouge, France. These devices are capable of receiving software instructions by telemetry, storing them in memory, and then executing those instructions to perform the functions described above in implementing the present invention, including the use of the minute ventilation signal acquired by the existing devices. The creation of suitable software instructions for controlling an implant to perform the aforementioned functions of the present invention are believed to be within the abilities of a person of ordinary skill in the art.

The circuits for sensing a minute ventilation signal and an acceleration signal comprises substantially all of logic and hardware elements required to operate the sensors to sense the associated parameter and pro duce output signals corresponding to the sensed parameters, and to deliver signals utilizable by the main circuit of the implant. The main circuit includes a microprocessor and memory (RAM and/or ROM), as well as conventional latches, registers and power supplies (not shown) for processing the output signals provided by the respective sensors.

Furthermore, the preferred embodiment of the invention described herein is implemented in an architecture including a microprocessor having associated software instructions stored in memory (ROM) and analog and digital logic circuits that are themselves known. Such an architecture is, for example, employed in the aforementioned devices manufactured by ELA Medical employing dual chamber cardiac pacing capabilities.

Although it does not present all of the advantages of the preferred solution with a microprocessor, a design in hard-wired discrete circuits having dedicated logic circuits is nevertheless perfectly foreseeable, and equally within the framework of the present invention.

One skilled in the art will appreciate that the present invention can be practiced by other than the described embodiments, which are presented for purposes of illustration and not of limitation.

We claim:

1. An active medical device, comprising:
   (a) means for measuring a physiological parameter of a patient and delivering a physiological signal;
   (b) means for detecting an awakening phase and a sleep phase of the patient, including: a first comparator means for computing an average value of the measured physiological signal over a first period, and comparing said average with a predetermined physiological threshold; and
   (c) means for indicating a first state of the patient as an awakening state in response to the average being greater than said physiological threshold, and as a sleep state otherwise;
   (d) means for measuring an activity parameter of the patient and producing a physical signal corresponding to said activity parameter;
   (e) second comparator means for comparing the measured physical signal with a predetermined activity threshold; and
   (f) means for indicating a second state of the patient as an awakening state in response to said activity signal being greater than said activity threshold, and as a sleep state otherwise;
   (g) means for comparing the first state of the patient with the second state of the patient; and
   (h) anticipating means for selectively modifying the period of said first comparator means in response to a discordance between the aforementioned first and second states of awakening or sleep.

2. The device of claim 1, wherein the physiological parameter measuring means further comprises a minute-ventilation signal and the period comprises a first number of preceding respiratory cycles.

3. The device of claim 1, wherein the period is a first plurality of prior periods and the anticipating means further comprises means for modifying the first plurality of prior periods.

4. The device of claim 3, wherein the anticipating means further comprises means for reducing the first plurality of prior periods to a second plurality less than the first plurality.

5. The device of claim 4, wherein the reducing means further comprises means for reducing the first plurality of prior periods by at least 50%.

6. The device of claim 4, wherein the physiological parameter measuring means further comprises a minute-ventilation signal and the first plurality of periods comprises a first plurality of preceding respiratory cycles.

7. The device of claim 4, further comprising means for determining a trend of the physiological signal as one of a stable, increasing and decreasing trend, wherein the reducing means further comprises means for selectively reducing the first plurality of periods:

in response to the first state being an awakening state, the second state being a sleep state, and a decreasing trend, or in response to the first state being a sleep state, the second state being an awakening state, and a stable or increasing trend.

8. The device of claim 1, wherein the activity parameter measuring means further comprises an acceleration sensor.

9. The device of claim 1, further comprising means for detecting a respiratory sleep disorder, said means being activated only in response to the first state being a sleep state.

10. The device of claim 9, wherein the sleep respiratory disorder detecting means further comprises means for detecting an apnea and for calculating an apnea index.

11. The device of claim 1, further comprising means for stimulating cardiac activity of a patient as a function of the measured physiological signal.

12. An active implantable medical device, comprising:

(a) a physiological sensor responsive to a physiological parameter of a patient having a first time response and a physiological output signal;

(b) a first a calculator responsive to said physiological output signal, a first period, and a predetermined physiological threshold, said calculator having an output corresponding to an average of successive values of the physiological signal over said period to provide an average physiological signal;

(c) a first state detector indicating a first state of the patient as an awakening state in response to the average physiological signal being greater than the physiological threshold, and as a sleep state otherwise;

(d) a patient activity sensor having a second response time and producing a physical signal output corresponding to an activity of the patient, the second response time being faster than said first response time;

(e) a second state detector for indicating a second state of the patient as an awakening state in response to said activity signal being greater than the activity threshold, and as a sleep state otherwise; and (f) a comparator responsive to the first state of the patient and the second state of the patient having a first output corresponding to a discordance of said first and second states;

wherein the first calculator response time is modified in response to a discordance between the first and second states of awakening or sleep.

13. The device of claim 12, wherein the physiological sensor further comprises a minute-ventilation sensor and the physiological output signal comprises a minute ventilation signal and the period comprises a first number of preceding respiratory cycles.

14. The device of claim 12, wherein period comprises a number of prior periods and modifying said period comprises reducing said number of prior periods.

15. The device of claim 14, wherein the number of prior periods is reduced by at least 50%.

16. The device of claim 14, wherein the physiological sensor further comprises a minute-ventilation sensor and the physiological output signal comprises a minute ventilation signal and the number of prior periods comprises a number of preceding respiratory cycles.

17. The device of claim 13 further comprising a physiological trend indicator having an output responsive to a trend of the physiological signal over time, said output being one of a stable, increasing or decreasing trend, wherein the number of prior periods is reduced:

in response to the first state being an awakening state, the second state being a sleep state, and a decreasing trend, or in response to the first state being a sleep state, the second state being an awakening state, and a stable or increasing trend.

18. The device of claim 12, wherein the activity sensor further comprises an acceleration sensor.

19. The device of claim 12, further comprising a respiratory sleep disorder detector that is activated only in response to the first state being a sleep state.

20. The device of claim 19, wherein the sleep respiratory disorder detector further comprises an apnea detector, a timer, and a counter for calculating an apnea index as a number of apneas per hour.

* * * * *

UNITED STATES PATENT AND TRADEMARK OFFICE
CERTIFICATE OF CORRECTION

| | | |
|---|---|---|
| PATENT NO. | : 6,773,404 B2 | Page 1 of 1 |
| APPLICATION NO. | : 10/310689 | |
| DATED | : August 10, 2004 | |
| INVENTOR(S) | : Poezevera et al. | |

It is certified that error appears in the above-identified patent and that said Letters Patent is hereby corrected as shown below:

TITLE PAGE

IN THE ABSTRACT

Line 8, "cycle" should be changed to --cycles--.

IN THE SPECIFICATION

Column 2, line 13, "analyse" should be changed to --analyze--; lines 45–46, "analysed" should be changed to --analyzed--.

Column 3, lines 40–41, "predominately" should be changed to --predominantly--.

Column 5, lines 23–24, between "VE128" and "The signal," insert --.--.

Column 6, line 7, after "two signals" and before "signal MV," insert --,--.

Column 7, line 61, "pro duce" should be changed to --produce--.

IN THE CLAIMS

Claim 12, line 5, "a first a calculator" should be changed to --a first calculator--.

Claim 14, line 1, before "period," insert --said--.

Signed and Sealed this
Eleventh Day of October, 2011

David J. Kappos
*Director of the United States Patent and Trademark Office*

UNITED STATES PATENT AND TRADEMARK OFFICE
CERTIFICATE OF CORRECTION

PATENT NO. : 6,773,404 B2
APPLICATION NO. : 10/310689
DATED : August 10, 2004
INVENTOR(S) : Poezevera et al.

It is certified that error appears in the above-identified patent and that said Letters Patent is hereby corrected as shown below:

TITLE PAGE

IN THE ABSTRACT

Line 8, "cycle" should be changed to --cycles--.

IN THE SPECIFICATION

Column 2, line 13, "analyse" should be changed to --analyze--; lines 45–46, "analysed" should be changed to --analyzed--.

Column 3, lines 40–41, "predominately" should be changed to --predominantly--.

Column 5, lines 23–24, between "VE128" and "The signal," insert --.--.

Column 6, line 7, after "two signals" and before "signal MV," insert --,--.

Column 7, line 61, "pro duce" should be changed to --produce--.

IN THE CLAIMS

Column 9, line 29 (Claim 12, line 5) "a first a calculator" should be changed to --a first calculator--.

Column 10, line 14 (Claim 14, line 1) before "period," insert --said--.

This certificate supersedes the Certificate of Correction issued October 11, 2011.

Signed and Sealed this
Eighth Day of November, 2011

David J. Kappos
*Director of the United States Patent and Trademark Office*